(12) United States Patent
Collins et al.

(10) Patent No.: US 6,785,614 B1
(45) Date of Patent: Aug. 31, 2004

(54) END SEQUENCE PROFILING

(75) Inventors: Colin Collins, San Rafael, CA (US); Stanislav Volik, Albany, CA (US); Joe W. Gray, San Francisco, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 09/586,529

(22) Filed: May 31, 2000

(51) Int. Cl.[7] .......................... C12Q 1/68; G06F 19/00; G01N 33/48; G01N 33/50
(52) U.S. Cl. ............................................. 702/20; 435/6
(58) Field of Search ................................ 435/6; 702/19

(56) References Cited

U.S. PATENT DOCUMENTS 5,830,645 A   11/1998   Pinkel et al.
6,013,439 A    1/2000   Lishanski et al.

OTHER PUBLICATIONS

Database Medline, DN 20311374. Knight S et al. Journal of Medical Genetics, (Jun. 2000) 37 (6) 401–409.*
Database Medline, DN 20232004. Mitelman et al. Mutation Research, (Apr. 2000) 462 (2–3) 247–53.*
Database Medline, DN 98407942. Kleinjan et al. Human Molecular Genetics, (1998) 7 (10) 1611–8.*
Database Medline, DN 96342101. Eppig et al. Current Opinion in Genetics and Development, (Dec. 1995) 5 (6) 709–716.*
Kelley J. et al. Nucleic Acid Research, 1997, 27(6), 1539–1546.*
Roach J. etal. Genomics, 1995, 26, 345–353.*
Brosch, R. et al., "Use of a Mycobacterium tuberculosis H37Rv Bacterial Artificial Chromosome Library for Genome Mapping, Sequencing, and Comparative Genomics," *Infection and Immunity*, 66(5):2221–2229 (1998).

Gray and Collins, "Genome changes and gene expression in human solid tumors," *Carcinogenesis*, 21(3):443–452 (2000).
Kallioniemi, A. et al., "Comparative Genomic Hybridization for Molecular Cytogenetic Analysis of Solid Tumors," *Science*, 258:818–821 (1992).
Mahairas, G.G., et al., "Sequence–tagged connectors: A sequence approach to mapping and scanning the human genome," *Proc. Natl. Acad. Sci. USA*, 96:9739–9744 (1999).
Mercer et al., "The Establishment of a Genetic Map of Orf Virus Reveals a Pattern of Genomic Organization That is Highly Conserved among Divergent Poxviruses," *Virology*, 212:698–704 (1995).
Philipp, W.J., et al., "Physical mapping of *Mycobacterium bovis* BCG Pasteur reveals differences from the genome map of *Mycobacterium tuberculosis* H37Rv and from *M. bovis*," *Microbiology*, 142:3135–3145 (1996).
Venter, J.C. et al., "A new strategy for genome sequencing," *Nature*, 381:364–366 (1996).
Altschul, S.F., et al., "Basic Alignment Search Tool," *J. Mol. Biol.*, 215(3):403–10 (Oct. 5, 1990).

* cited by examiner

*Primary Examiner*—Michael Borin
(74) *Attorney, Agent, or Firm*—Townsend and Townsend and Crew LLP

(57) ABSTRACT

The present invention provides a novel method to identify rearrangements in a test genome, e.g., a tumor genome, when compared to a reference genome. This method provides major improvements over previous methods in terms of efficiency, rapidity, and cost-effectiveness. Briefly, this method involves generating or obtaining a large insert vector library from a test genome, sequencing the ends of the inserts in the library, and comparing the co-linearity of the sequenced ends in the library with corresponding sequences within a substantially-sequenced reference genome. This invention is useful for any of a number of applications, including for identifying rearrangements in tumor genomes and for determining genetic differences between closely related species as well as between different strains of the same species.

24 Claims, No Drawings

END SEQUENCE PROFILING

FIELD OF THE INVENTION

The present invention relates to methods of comparative genomic analysis. Specifically, the invention provides a novel method to rapidly identify rearrangements within a test genome, e.g., a tumor genome, in comparison with a substantially-sequenced reference genome.

BACKGROUND OF THE INVENTION

The ability to compare related genomes has long been a major goal of biological research. For example, because tumor genomes are known to have many rearrangements (e.g., amplifications, deletions, transpositions, translocations, episomes and double minutes) that can contribute to tumor progression, the ability to identify such rearrangements by comparing tumor genomes with normal genomes would allow the identification of cancer-causing genetic alterations. Indeed, numerous cancer genes have been identified on the basis of their localization to specific chromosomal rearrangements. In addition, closely related species, or even different individuals or strains within a single species, can differ by virtue of genomic rearrangements that can play important roles in causing the phenotypic differences between the species or strains. Thus, the identification of genes affected by rearrangements between species or strains would allow the identification of genetic events that accompany speciation or the establishment of strain-specific phenotypic differences. In each of these cases, genomic rearrangements can produce profound effects on a cell or individual because they result in, e.g., gene mutation, deletion, or the creation of novel chimeric genes with altered or enhanced function. The identification of genes that are affected by such rearrangements would thus enable, inter alia, the development of useful diagnostic and prognostic markers, and would suggest targets for therapeutic intervention (see, e.g., Ehrlich, M. (2000) *DNA Alterations in Cancer, Genetic and Epipenetic Changes*. Eaton Publishing, Natick, Mass.).

Traditionally, efforts to compare related genomes has relied either on the comparison of individual sequences within the genomes, or on the detection of rearrangements based on cytogenetic analysis, including traditional cytogenetic methods based on, e.g., G-banding, silver staining (NOR), and C-banding, as well as more recent tools such as fluorescence in situ hybridization (FISH), representational difference analysis (RDA), restriction landmark genome scanning (RLGS), high-throughput loss of heterozygosity (LOH) and comparative genome hybridization (CGH; see, Kallioniemi et al. (1992) *Science* 258: 818–21) (see, e.g., Gray and Collins, (2000) *Carcinogenesis* 21:443–452).

While each of these widely-used methods have enabled significant advances, none of them, however, provides a high-resolution method for rapidly, efficiently, and systematically identifying any type of rearrangement within a test genome in comparison to a sequenced referenced genome. Further, this deficiency is currently becoming more and more acute because of the large number of genome sequences that have already been determined, and because of the even larger number of genome projects that are still in progress. While the availability of genome sequences for virtually any organism will soon allow the systematic sequence-based comparison of related genomes, the only currently-available method for doing this requires the complete sequencing of each genome involved in the comparison. While such comparisons will thus be technically possible, the cost of sequencing an entire genome will remain a significant impediment to such studies for the foreseeable future. Clearly, there is a great need for new and more efficient sequence-based approaches for the comparison of related genomes. The present invention addresses these and other needs.

SUMMARY OF THE INVENTION

The present invention provides a novel method for identifying rearrangements in a test genome, e.g., a tumor genome, when compared to a reference genome. This method represents a major improvement over previous methods in terms of efficiency, rapidity, and cost-effectiveness. The present method involves generating a library from a test genome, sequencing the ends of the inserts in the library, and comparing the co-linearity of the sequenced ends in the library with corresponding sequences in a reference genome. This invention is useful for any of a number of applications, including for the identification of rearrangements within tumor genomes, between closely related species, and between different strains of the same species.

In one aspect, the present invention provides a method for comparing a test genome to a reference genome, the method comprising (i) providing a plurality of clones of known size that substantially cover at least a portion of the test genome; (ii) obtaining sequence information from the termini of each of the plurality of clones; (iii) identifying a pair of sequences within the reference genome that corresponds to each pair of terminal sequences; and (iv) determining the relationship between the members of each pair of corresponding sequences within the reference genome; wherein a difference in the observed relationship between the members of any of the pairs of corresponding sequences within the reference genome and the expected relationship based upon the known size of the plurality of clones indicates the presence of a rearrangement in the test genome compared to the reference genome.

In one embodiment, the method further comprises determining the sequence of the test genome over a region spanning at least one breakpoint of the rearrangement. In another embodiment, the reference genome is a human genome. In another embodiment, the test genome is from a tumor cell. In another embodiment, the reference genome and the test genome are from difference species. In another embodiment, the plurality of clones covers substantially all of the test genome.

In another embodiment, the members of at least one pair of corresponding sequences within the reference genome are closer together than expected based on the known size of the plurality of clones, indicating the presence of an insertion in the test genome between the pair of terminal sequences. In another embodiment, the members of at least one pair of corresponding sequences within the reference genome are further apart than expected based on the known size of the plurality of clones, indicating the presence of a deletion in the test genome between the pair of terminal sequences. In another embodiment, the members of at least one pair of corresponding sequences within the reference genome are present on different chromosomes in the reference genome, indicating the presence of a translocation in the test genome between the pair of terminal sequences. In another embodiment, the method further comprises determining the frequency of each of the terminal sequences, wherein a change in the relative frequency of any of the terminal sequences indicates the presence of an amplification or a deletion in the test genome that includes the terminal sequence. In another embodiment, at least one member of at least one pair of terminal sequences in the test genome is present at a greater than expected frequency in the plurality of clones, indicating the presence of an amplification in the test genome that includes the at least one member of the at least one pair of terminal sequences. In another embodiment, at least one member of at least one pair of terminal sequences in the test genome is present at a lower than expected frequency in the plurality of clones, indicating the presence of a deletion in the test genome that includes the at least one member of the at least one pair of terminal sequences.

In another embodiment, the plurality of clones are BAC clones. In another embodiment, the plurality of clones are PAC clones. In another embodiment, the plurality of clones represents a redundancy of at least about 10 fold of the test genome or the portion of the test genome. In another embodiment, the plurality of clones represents a redundancy of at least about 20 fold of the test genome or the portion of the test genome. In another embodiment, the terminal sequences are present on average between about every 5 kb to about every 500 kb throughout the test genome or the portion of the test genome. In another embodiment, the terminal sequences are present on average every 50 kb or less throughout the test genome or the portion of the test genome. In another embodiment, the terminal sequences are present on average every 10 kb or less throughout the test genome or the portion of the test genome. In another embodiment, the terminal sequences are present on average every 5 kb or less throughout the test genome or the portion of the test genome. In another embodiment, the reference genome is a human genome and the plurality of clones comprises at least about 50,000, 100,000, 200,000, 250,000, or more clones. In another embodiment, the terminal sequences are determined by automated sequencing. In another embodiment, the pairs of terminal sequences from the test genome are compared to the pairs of corresponding sequences within the reference genome using a computer.

DESCRIPTION OF THE SPECIFIC EMBODIMENTS

I. Introduction

The present invention provides a novel, rapid and cost-effective method to identify rearrangements in a test genome, e.g., a tumor genome, when compared to a reference genome. Briefly, the present method involves generating or obtaining a large insert vector library from a test genome, sequencing the ends of the inserts in the library, and comparing the relationship between each pair of sequenced ends in the library with a pair of corresponding sequences in a substantially-sequenced reference genome.

Typically, to perform ESP, an approximately 10–30 fold redundant library, e.g., a BAC library, is generated using genomic DNA from a test genome, e.g., a tumor genome. The library is comprised of clones with genomic inserts of, e.g., 50–200 kb, preferably 150–200 kb in length, arrayed, for example, in multi-well microtiter plates. Several hundred, e.g., about 600, base pairs of sequence from each end of the clones are determined and computationally aligned to the normal sequence. The termini should fall every 500, 100, 50, 25, 10, 5, or fewer kb, on average, throughout the genome. In non-rearranged regions of the genome, the relationship between the members of each pair of end sequences will be similar to the relationship between corresponding sequences in the normal reference genome, and the frequency of each terminal sequence, and of each pair of sequences, will be close to that statistically expected for the normal genome copy-number. Deviations in frequency, order, or spacing of the terminal sequences, however, will reveal rearrangements (e.g., deletions, translocations, amplifications, insertions, and inversions). For example, the two ends of an insert spanning a translocation breakpoint will map to different parts of the reference genome and will indicate the precise genomic locations of the translocated sequences.

Since ESP obviates the need for complete resequencing of a test genome, it is faster and more cost efficient than previous methods (at least two orders of magnitude cheaper for a mammal-sized genome).

In cancer, ESP will allow the identification of, e.g., amplifications, translocations, inversions, transpositions, homozygous deletions, regulatory elements, oncogenes, tumor suppressor genes and chimeric cancer genes that contribute to tumor progression, e.g., genes and regulatory elements involved in cancer development, progression and resistance to therapy. In addition, ESP of tumor genomes will allow the elucidation of the mechanisms and specific sequence elements underlying gene amplification. Further, multi-tumor whole genome comparative analysis will identify minimum recurrent genome abnormalities, thus pinpointing cancer genes with unprecedented resolution and speed. ESP will thus have a profound impact on development of diagnostics (especially chip based) and therapeutics and may ultimately lead to individualized whole-tumor genome ESP analysis in a clinical setting.

Because ESP involves the direct comparison of a large number of sequences from a tumor genome and corresponding sequences within a reference genome, an additional outcome of ESP analysis will be the identification of single nucleotide polymorphisms in tumors and the direct measurement of mutation rate in different tumor types.

Other applications of ESP technology include the identification of genomic changes that produce differences between closely related microorganisms, plants, domestic animals and important pests/parasites. These genomic changes will reveal genes and regulatory regions of significant economic and humanitarian value. For example, ESP applied to primate genome analysis will allow the tracking of genomic changes underlying human speciation. Such information might be important for understanding the molecular basis of human developmental disorders Once a rearrangement has been identified using ESP, in a tumor genome or any other test genome, the sequence spanning the rearrangement is typically determined, thereby allowing the identification of mutations, deletions, and chimeric genes that underlie the cancer progression or that otherwise account for differences between the test and reference genomes.

II. Definitions

A "test genome" refers to any collection of nucleic acids representative of a genome or a portion of a genome. The collection will typically be a collection of sequences derived directly from genomic DNA, but can be any set of nucleic acids that are representative of the genome, including, e.g., mRNA or cDNA. Typically, a test genome is or can be entirely or partially present in a large-insert library. A "test genome" can represent a genome from any organism or species, including viruses, prokaryotic and, preferably, eukaryotic species, including protozoa, fungi, plants, and animals. A "test genome" can be from the same or a different species as the reference genome. If from the same species, a test genome can represent, e.g., an individual with a disease or condition such as cancer that is associated with genomic rearrangements, and the methods are performed to determine the location and nature of the rearrangements. The test genome can also represent a randomly selected member of the same species, and the methods are performed to simply identify genetic variation within a species. Further, a test genome can represent a different strain of the same species, e.g., a different strain of an agriculturally significant species, and the methods are performed to identify genetic changes underlying the phenotypic differences between the strain and a reference strain. Alternatively, in numerous embodiments, the test genome-is from a different, usually closely-related, species as the reference genome, and the methods are performed to identify genomic differences between the species. In one such embodiment, the methods are performed to compare the genomes of humans and a higher primate species, e.g., chimpanzees, to identify alterations that occurred during human evolution. In any of the herein-described embodiments, the test genome can be derived from a living organism, i.e. the DNA is obtained from a biological sample taken directly from the organism, or can be derived from a preexisting biological sample, e.g., a cultured cell line.

A "reference genome" is a collection of nucleic acids or sequence information that is representative of a second genome to which a test genome is compared. Typically, a "reference genome" is from an organism or a species whose genome has been at least substantially sequenced, and for which the sequence is recorded in a format that allows its comparison with terminal sequences obtained from a test genome library, such as in a database that is searchable using software based on an algorithm such as BLAST.

A genome that has been "substantially sequenced" means that at least a portion of the genome has been sequenced to a degree that allows its comparison with terminal sequences from a test genome library. For example, an organism of which only a single chromosome, or a defined portion of a single chromosome, has been sequenced, can serve as a reference genome because ESP can be performed to determine rearrangements within a test genome that correspond to that chromosome or chromosomal portion. In addition, while a high level of confidence in a sequence is preferable, the presence of gaps or low confidence regions, e.g., in a genome sequenced in "draft" form, can still serve as a reference genome so long that a sufficient number of the terminal sequences will have matches in the reference genome sequence database to allow useful comparison.

To "compare," or to make a "comparison," between a test genome and a reference genome means that the relationship between the members of at least one pair of terminal sequences from a library made using the test genome is compared to the relationship between corresponding sequences within a reference genome. Thus, a comparison can be made even when only a portion of the test genome has been cloned, and even when only a portion of the reference genome has been sequenced, so long as enough of the reference genome has been sequenced to allow the identification of sequences within the reference genome that correspond to at least one pair of terminal sequences from the test genome, and to allow a determination of the physical relationship between the corresponding sequences within the reference genome.

When sequences within a reference genome are said to "correspond" to a terminal sequence, or to be "homologous" or "corresponding" to a terminal sequence, this indicates that the sequence within the reference genome occupies an evolutionary equivalent position within the genome. For example, in the absence of any rearrangements, a test genome from an individual of the same species as the reference genome will contain essentially equivalent sequences at essentially equivalent positions within the genome. Each of the sequences within the test genome, therefore, has a "corresponding" sequence within the reference genome, present at an equivalent genomic location. If a rearrangement has occurred within the test genome, however (e.g., due to cancer-associated genomic instability or to a speciation-associated genomic alteration), the relationship between sequences spanning the rearrangement within the test genome, and "corresponding" sequences within the reference genome, may be altered. For example, an insertion of 100 kb into a test genome will create an increase of 100 kb between two genes spanning the insertion when compared to the distance between corresponding sequences in the reference genome. Similarly, a translocation within a test genome will cause "corresponding" sequences within the reference genome to be localized to different chromosomes, i.e., the chromosomes involved in the translocation. Typically, according to the present invention, "corresponding" sequences are identified by virtue of sequence homology, i.e., the sequence within the reference genome with the highest percent sequence identity to the terminal sequence will be considered to be the "corresponding" sequence. For example, a sequence within the reference genome that is found to be identical to a terminal sequence will usually be interpreted to be the corresponding sequence. In some cases, additional information can be relied upon to identify corresponding sequences. For example, a finding that two candidate corresponding sequences from a reference genome are separated by an equivalent distance within the reference genome as the distance between the two terminal sequences that the candidate sequences apparently correspond to (i.e., the distance corresponding to the size of the vector insert) provides strong evidence that the two sequences within the reference genome do in fact "correspond" to the terminal sequences.

The "relationship" between the members of any pair of sequences, e.g., terminal sequences or corresponding sequences, refers to the relative position of the sequences within, e.g., a genome or a library. For example, the relationship can refer to the physical or genetic distance between the two sequences, whether the two sequences are present within the same vector or on the same chromosome, etc.

The terms "isolated," "purified," or "biologically pure" refer to material that is substantially or essentially free from components that normally accompany it as found in its native state. Purity and homogeneity are typically determined using analytical chemistry techniques such as polyacrylamide gel electrophoresis or high performance liquid chromatography. The term "purified" denotes that a nucleic acid or protein gives rise to essentially one band in an electrophoretic gel. Particularly, it means that the nucleic acid or protein is at least 85% pure, more preferably at least 95% pure, and most preferably at least 99% pure.

"Nucleic acid" refers to deoxyribonucleotides or ribonucleotides and polymers thereof in either single- or double-stranded form. The term encompasses nucleic acids containing known nucleotide analogs or modified backbone residues or linkages, which are synthetic, naturally occurring, and non-naturally occurring, which have similar binding properties as the reference nucleic acid, and which are metabolized in a manner similar to the reference nucleotides. Examples of such analogs include, without limitation, phosphorothioates, phosphoramidates, methyl phosphonates, chiral-methyl phosphonates, 2-O-methyl ribonucleotides, peptide-nucleic acids (PNAs).

Unless otherwise indicated, a particular nucleic acid sequence also implicitly encompasses conservatively modified variants thereof (e.g., degenerate codon substitutions) and complementary sequences, as well as the sequence explicitly indicated. Specifically, degenerate codon substitutions may be achieved by generating sequences in which the third position of one or more selected (or all) codons is substituted with mixed base and/or deoxyinosine residues (Batzer et al., *Nucleic Acid Res.* 19:5081 (1991); Ohtsuka et al., *J. Biol. Chem.* 260:2605–2608 (1985); Rossolini et al., *Mol. Cell. Probes* 8:91–98 (1994)). The term nucleic acid is used interchangeably with gene, cDNA, mRNA, oligonucleotide, and polynucleotide.

With respect to particular nucleic acid sequences, "conservatively modified variants" refers to those nucleic acids which encode identical or essentially identical amino acid sequences, or where the nucleic acid does not encode an amino acid sequence, to essentially identical sequences. Because of the degeneracy of the genetic code, a large number of functionally identical nucleic acids encode any given protein. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations," which are one species of conservatively modified variations. Every nucleic acid sequence herein which encodes a polypeptide also describes every possible silent variation of the nucleic acid. One of skill will recognize that each codon in a nucleic acid (except AUG, which is ordinarily the only codon for methionine, and TGG, which is ordinarily the only codon for tryptophan) can be modified to yield a functionally identical molecule. Accordingly, each silent variation of a nucleic acid which encodes a polypeptide is implicit in each described sequence.

A "label" is a composition detectable by spectroscopic, photochemical, biochemical, immunochemical, or chemical means. For example, useful labels include $^{32}P$, fluorescent dyes, electron-dense reagents, enzymes (e.g., as commonly used in an ELISA), biotin, digoxigenin, or haptens and proteins for which antisera or monoclonal antibodies are available.

As used herein a "nucleic acid probe or oligonucleotide" is defined as a nucleic acid capable of binding to a target nucleic acid of complementary sequence through one or more types of chemical bonds, usually through complementary base pairing, usually through hydrogen bond formation. As used herein, a probe may include natural (i.e., A, G, C, or T) or modified bases (7-deazaguanosine, inosine, etc.). In addition, the bases in a probe may be joined by a linkage other than a phosphodiester bond, so long as it does not interfere with hybridization. Thus, for example, probes may be peptide nucleic acids in which the constituent bases are joined by peptide bonds rather than phosphodiester linkages. It will be understood by one of skill in the art that probes may bind target sequences lacking complete complementarity with the probe sequence depending upon the stringency of the hybridization conditions. The probes are preferably directly labeled as with isotopes, chromophores, lumiphores, chromogens, or indirectly labeled such as with biotin to which a streptavidin complex may later bind. By assaying for the presence or absence of the probe, one can detect the presence or absence of the select sequence or subsequence.

A "labeled nucleic acid probe or oligonucleotide" is one that is bound, either covalently, through a linker or a chemical bond, or noncovalently, through ionic, van der Waals, electrostatic, or hydrogen bonds to a label such that the presence of the probe may be detected by detecting the presence of the label bound to the probe.

The term "recombinant" when used with reference, e.g., to a cell, or nucleic acid, protein, or vector, indicates that the cell, nucleic acid, protein or vector, has been modified by the introduction of a heterologous nucleic acid or protein or the alteration of a native nucleic acid or protein, or that the cell is derived from a cell so modified. Thus, for example, recombinant cells express genes that are not found within the native (non-recombinant) form of the cell or express native genes that are otherwise abnormally expressed, under expressed or not expressed at all.

A "promoter" is defined as an array of nucleic acid control sequences that direct transcription of a nucleic acid. The term "operably linked" refers to a functional linkage between a nucleic acid expression control sequence (such as a promoter, or array of transcription factor binding sites) and a second nucleic acid sequence, wherein the expression control sequence directs transcription of the nucleic acid corresponding to the second sequence.

The term "heterologous," "hybrid," or "chimeric," when used with reference to a nucleic acid or polypeptide, indicates that the nucleic acid or polypeptide comprises two or more subsequences that are not found in the same combination in nature, e.g., a nucleic acid comprising a promoter from one source and a coding region from another source, or a nucleic acid (or encoded fusion protein) comprising a coding sequence that comprises, in frame, portions of two or more previously-separated open reading frames. Such nucleic acids or polypeptides can be recombinantly produced, or, alternatively, can result from one or more genomic rearrangements that have linked two or more previously separated subsequences.

An "expression vector" is a nucleic acid construct, generated recombinantly or synthetically, with a series of specified nucleic acid elements that permit transcription of a particular nucleic acid in a host cell. The expression vector can be part of a plasmid, virus, or nucleic acid fragment. Typically, the expression vector includes a nucleic acid to be transcribed operably linked to a promoter.

The terms "identical" or percent "identity," in the context of two or more nucleic acids or polypeptide sequences, refer to two or more sequences or subsequences that are the same or have a specified percentage of amino acid residues or nucleotides that are the same (i.e., 60% identity, preferably 65%, 70%, 75%, 80%, 85%, 90%, or 95% identity over a specified region), when compared and aligned for maximum correspondence over a comparison window, or designated region as measured using one of the following sequence comparison algorithms or by manual alignment and visual inspection. Such sequences are then said to be "substantially identical." This definition also refers to the compliment of a test sequence. Preferably, the identity exists over a region that is at least about 25 amino acids or nucleotides in length, or more preferably over a region that is 50–100 amino acids or nucleotides in length.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated.

Default program parameters can be used, or alternative parameters can be designated. The sequence comparison algorithm then calculates the percent sequence identities for the test sequences relative to the reference sequence, based on the program parameters. For sequence comparison of nucleic acids and proteins, the BLAST and BLAST 2.0 algorithms and the default parameters discussed below are preferably used.

A "comparison window", as used herein, includes reference to a segment of any one of the number of contiguous positions selected from the group consisting of from 20 to 600, usually about 50 to about 200, more usually about 100 to about 150 in which a sequence may be compared to a reference sequence of the same number of contiguous positions after the two sequences are optimally aligned. Methods of alignment of sequences for comparison are well-known in the art. Optimal alignment of sequences for comparison can be conducted, e.g., by the local homology algorithm of Smith & Waterman, *Adv. Appl. Math.* 2:482 (1981), by the homology alignment algorithm of Needleman & Wunsch, *J. Mol. Biol.* 48:443 (1970), by the search for similarity method of Pearson & Lipman, *Proc. Nat 'l. Acad. Sci.* USA 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection (see, e.g., *Current Protocols in Molecular Biology* (Ausubel et al., eds. 1995 supplement)).

A preferred example of algorithm that is suitable for determining percent sequence identity and sequence similarity are the BLAST and BLAST 2.0 algorithms, which are described in Altschul et al., *Nuc. Acids Res.* 25:3389–3402 (1977) and Altschul et al., *J. Mol. Biol.* 215:403–410 (1990), respectively. BLAST and BLAST 2.0 are used, with the parameters described herein, to determine percent sequence identity for the nucleic acids and proteins of the invention. Software for performing BLAST analyses is publicly available through the National Center for Biotechnology Information (http://www.ncbi.nlm.nih.gov/). This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., supra). These initial neighborhood word hits act as seeds for initiating searches to find longer HSPs containing them. The word hits are extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) of 10, M=5, N=−4 and a comparison of both strands. For amino acid sequences, the BLASTP program uses as defaults a wordlength of 3, and expectation (E) of 10, and the BLOSUM62 scoring matrix (see Henikoff & Henikoff, *Proc. Natl. Acad. Sci.* USA 89:10915 (1989)) alignments (B) of 50, expectation (E) of 10, M=5, N=−4, and a comparison of both strands.

The BLAST algorithm also performs a statistical analysis of the similarity between two sequences (see, e.g., Karlin & Altschul, *Proc. Nat . Acad. Sci.* USA 90:5873–5787 (1993)). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.2, more preferably less than about 0.01, and most preferably less than about 0.001.

An indication that two nucleic acid sequences or polypeptides are substantially identical is that the polypeptide encoded by the first nucleic acid is immunologically cross reactive with the antibodies raised against the polypeptide encoded by the second nucleic acid, as described below. Thus, a polypeptide is typically substantially identical to a second polypeptide, for example, where the two peptides differ only by conservative substitutions. Another indication that two nucleic acid sequences are substantially identical is that the two molecules or their complements hybridize to each other under stringent conditions, as determined using standard methods (see, e.g., Ausubel or Sambrook, infra). Yet another indication that two nucleic acid sequences are substantially identical is that the same primers can be used to amplify the sequence.

By "host cell" is meant a cell that contains an expression vector and supports the replication or expression of the expression vector. Host cells may be prokaryotic cells such as *E. coli*, or eukaryotic cells such as yeast, insect, amphibian, or mammalian cells such as CHO, HeLa and the like, e.g., cultured cells, explants, and cells in vivo.

III. Library Construction

This invention relies on routine techniques in the field of molecular biology. Basic texts disclosing the general methods of use in this invention include Sambrook et al., *Molecular Cloning, A Laboratory Manual* (2nd ed. 1989); Kriegler, *Gene Transfer and Expression: A Laboratory Manual* (1990); and *Current Protocols in Molecular Biology* (Ausubel et al., eds., 1994)). For nucleic acids, sizes are given in either kilobases (kb) or base pairs (bp). These are estimates derived, e.g., from agarose or acrylamide gel electrophoresis, from sequenced nucleic acids, or from published DNA sequences.

It will be appreciated that any of the individual steps required for the practice of ESP, e.g., DNA isolation, the preparation of large-insert vectors such as BACs, the cloning of DNA fragments into the vectors, the maintenance and propagation of the library, the isolation of vector DNA, the sequencing of insert termini, and the analysis of the terminal sequences in comparison with a reference genome, can be practiced using any of a large number of standard methods. Further, many of the steps (e.g., library preparation, end-sequencing, etc.) can be performed by any of a large number of commercial suppliers. Preferably, the steps are performed using automated systems, e.g., for DNA preparation, end sequencing, and analysis of the sequence, allowing the rapid and efficient practice of the methods. Information regarding methodology for making, obtaining, and using BAC, PAC, and other vectors, for performing high-throughput DNA sequencing, for sequence analysis, etc. is available from any of a large number of sources, for example the Internet sites of any genome center, e.g., the Genome Analysis core facility at the UCSF Comprehensive Cancer Center, The Human Genome Program at the U.S. Department of Energy and at the National Institutes of Health, the Sanger Center, the Human Genome Organization, Baylor College of Medicine Human Genome Center, Columbia University Genome Center, the National Center for Genome Resources, Stanford Human Genome Center, the University of Oklahoma's Advanced Center for Genome Technology, the University of Washington Department of Molecular Biotechnology, Washington University Genome Sequencing Center, Roswell Park Cancer Institute, the Whitehead Institute Center for Genome Research (at MIT), the Institute for Genomic Research, CalTech's Genome Research Laboratory, the Clemson University Genomics Institute, and others, and is also available from any of a large number of commercial suppliers, for example, Genome Therapeutics Corporation, Research Genetics, Incyte Genomics, Genset, Celera Genomics, SeqWright, Southwest Scientific Resources, Gene Alliance, and others.

The library of inserts can include sequences representative of the genome, or a particular portion thereof, e.g., a particular chromosome, a particular set of chromosomes, a particular portion of one or more chromosomes, or any other collection of nucleic acids such as a cDNA library. The genome from which the library is made is referred to as the "test genome," which is compared to a substantially-sequenced "reference genome." It is important to note that the library used in ESP can be prepared expressly for use in the herein-described methods, or can be a library prepared for any other purpose, including established, previously prepared libraries. For example, any of a large number of BAC or PAC libraries, available from, e.g., Caltech, Genome Systems, or Research Genetics, can readily be used to practice the present invention. (See, e.g., Mahairas, et al., (1999) Proc. Natl Acad. Sci. USA 96:9739–9744).

In numerous embodiments, the test genome and the reference genome will be from the same species, and the test genome will represent, e.g., an individual, a cell type, or a strain differing in one or more respects from the reference genome. In one preferred embodiment, the test genome is a genome from an individual with a disease or condition associated with genomic rearrangements. In a particularly preferred embodiment, the disease or condition is cancer, and the present methods are used to detect the genetic differences between a cancer cell and a reference genome representing a normal, cancer-free cell. In other embodiments, the test genome represents a strain or variant that is from the same species as the reference genome, e.g., the genomes of different plant varieties, or different animal varieties such as different dog types, are compared in order to identify genomic changes associated with one or more traits that differ between the varieties. In addition, the genome of a pathogenic organism can be compared with a reference genome that represents a non-pathogenic relative, in order to identify genetic alterations underlying the pathogenicity in the strain. In other embodiments, the genomes of related species can be compared, e.g., to identify genetic changes associated with speciation, or to identify the genetic changes underlying specific phenotypic differences between the species.

A. Isolating DNA from the Test Genome

To construct a library, nucleic acids (e.g., genomic DNA, cDNA or mRNA) are first extracted from a tissue (e.g., obtained by tissue biopsy), cell culture, or any other source of cells or nucleic acid. Typically, genomic DNA is used. In this case, the DNA is either mechanically sheared or enzymatically digested to yield large fragments suitable for cloning in a vector capable of containing large DNA fragments, e.g., >50 kb, preferably 100–200 kb, most preferably from about 150 to about 200 kb. Preferably, the DNA is partially digested using a limiting amount of a restriction enzyme, according to standard methodology.

Isolation of nucleic acids can be performed using any standard method, e.g., as taught in Ausubel or Sambrook, both supra. Cells derived from a tissue, e.g., a tumor, can be used either en masse, or can be clonally isolated to ensure maximum genetic homogeneity among the cells used to generate the library. Once cells representing a test genome are obtained, e.g., from a tissue or cell culture, the cells are lysed using any standard method, e.g., using a detergent. The lysis can be performed in conjunction with, or prior to, removal of non-DNA cellular components such as using proteases, RNAses, etc. Genomic DNA isolation, for example, can also be performed using any commercial product for the isolation of genomic DNA, such as the Wizard™ kit available from Promega or the Split Second™ DNA Preparation Kit from Roche.

Typically, insert DNA is size fractionated to ensure that only single, usually large inserts are ligated into the vectors. Such size fractionation can be performed using any method, such as sucrose gradient fractionation or, preferably, by gel electrophoresis (e.g., pulsed-field gel electrophoresis, or PFGE). Often, after a first size selection by pulsed-field gel electrophoresis, a second selection step is included to remove small DNA fragments trapped during the first round of PFGE.

In a preferred embodiment, large fragment genomic DNA is obtained by mixing cells representing the test genome with agarose and lysing the cells while in the agarose. Using this method, the DNA can be obtained with minimal handling, thus ensuring maximum yield of high molecular weight fragments. Further, once the cells have been lysed, numerous subsequent steps can be performed without removing the DNA from the agarose, including partially digesting the DNA with a restriction enzyme, e.g., an enzyme with a six nucleotide recognition site such as HindIII, removing the protein component of the DNA, e.g., with proteinase K, running the DNA on a gel, e.g., a pulsed-field gel, and excising the DNA corresponding to a desired size range (e.g., 100–200 kb). Subsequently, the DNA is obtained from the gel slice by digesting the agarose, e.g., with agarase, ligated with vector DNA, and introduced into host cells, e.g., E. coli host cells, by a method such as electroporation. See, e.g., Rondon et al., (1999) Proc. Natl. Acad. Sci. USA 96:6451–6455). Each of these steps is well known in the art.

In one embodiment, following size selection by gel electrophoresis, the DNA is removed directly from the agarose, e.g., by electroelution or by digestion of the agarose with agarase, and the remaining steps performed in the absence of agarose. Similarly, if DNA is size fractionated by sucrose gradient, the DNA is purified using standard methods and the remaining steps performed.

B. Vectors

Any of a variety of well known vectors can be used in the herein-described methods. Typically, large portions of genomes are compared, so vectors capable of containing large DNA inserts are preferably used, e.g., BACs (bacterial artificial chromosomes), PACs (P1-derived artificial chromosomes), YACs (yeast artificial chromosomes), MACs (mammalian artificial chromosomes), HACs (human artificial chromosomes), cosmids, P1 vectors, bacteriophage λ, or any other vector capable of containing large (e.g., at least about 15, 25, 50, 100, 150, or more kb). Preferably, the vectors are PAC or, most preferably, BAC vectors. Typically, the vectors include multiple elements such as multiple cloning sites for insertion of DNA fragments, appropriate primer sequences on either end of the multiple cloning site to allow sequencing the ends of the inserts (e.g., T7, SP6, T3, or M13 primer sites), selectable markers to allow selection of host cells that contain the vector, selectable genes to allow selection against cells containing vectors without an insert (e.g., sacBII, see, e.g., Pierce et al. (1992) Proc. Nal. Acad. Sci. USA 89:2056–2060), and recognition sites for extremely rare nucleases, e.g., the PI-Sce I nuclease, permitting linearization of the recombinant vector without cutting the insert sequences. In addition, the vectors can contain plasmid sequences, e.g., pUC sequences, to allow high copy number propagation of the vector when preparing the vector prior to ligation. Such pUC sequences are typically located within the polylinker, flanked by restriction sites, so that linearization of the vector prior to ligation removes the pUC sequences, thereby ensuring low copy number maintenance of the vector after ligation.

In numerous embodiments, the library is made using a BAC vector (see, e.g., Shizuya H. et. al. 1992, Proc. Natl. Acad. Sci. USA 89:8794–8797; Kim, et al. (1996) Genomics, 34, 213–218). BAC vectors are based on the E. coli fertility plasmid, or F-factor. The use of the F-factor replicon ensures strict, low copy number control of the clones, and, as a result, increased stability of the vectors. Bacteriophage P1-derived artificial chromosomes (PACs; see, e.g., Ioannou, et al, (1994) Nature Genet. 6:84–9; Ioannou et al. (1996)), which combine P1 and F-factor features, can also be used.

The basic structure of the BAC/PAC vectors is derived from the endogenous plasmid F. The F backbone contains four essential regions that function in plasmid stability and copy number (see, e.g., Willetts & Skurray (1980) Annu Rev Genet 14:41–76), including ParA and B, which are required for partitioning, plasmid stability, and incompatibility with other F factors, OriS, which is the origin of DNA replication, and RepE, which encodes protein E, which is required for replication from OriS and for copy number control.

Chloramphenicol resistance gene are also typically included for antibiotic selection of transformnants, as are LacZ markers. The original BAC vector, pBAC108L, does not include the LacZ gene for color selection, whereas pBeloBAC11 does, thereby allowing the color-based identification of recombinant clones.

Any of a number of BAC vectors can be used, including, but not limited to, pBeloBAC11 and pBAC108L (see, e.g., Shizuya et al. (1992) Proc. Natl. Acad. Sci. USA, 89:8794–8797; Kim et al. (1996) Genomics, 34:213–218), pECBAC1 (see, e.g., Frijters et al, Theor. Appl. Genet. (1997) 94:390–399, pINDIGO451, pEBAC140, and pBACe3.6 (available from the Roswell Park Cancer Institute (RPCI; bacpac.med.buffalo.edu)).

PAC vectors can also be used to practice ESP (see, e.g., Ioannou, et al, (1994) Nature Genet. 6:84–9; Ioannou et al. (1996)) Construction of Bacterial Artificial Chromosome Libraries using the modified P1 (PAC) System. In: Current Protocols in Human Genetics. Eds. Dracopoli et al. Unit 5.15 Pub. John Wiley and Sons, NY). PAC vectors have most of the features of the BAC system, and typically contain the SacB gene, encoding sucrose synthase, thus providing a positive selection for recombinant clones during library construction. Because of the SacB gene, when cells are grown in the presence of saccharose, the saccharose is degraded by the sucrose synthase into levan, which is highly toxic to E. coli. Because the BamHI cloning site is within the SacB gene, insertion of a large DNA fragment into the BamHI site disrupts the SacB gene, thereby allowing the cell to grow on media containing saccharose. Additionally the vector has a "pUC19-link", containing a high copy number origin of DNA replication, which is used for vector propagation and which is later removed during vector preparation for library construction. PAC vectors also contain other elements such as the P1 lytic replicon, the P1 plasmid replicon, and others.

A typical PAC vector is pPAC4, which contains the following elements: an origin of replication that is functional in E. coli cells from P1 phage (the P1 replicon), generating a low copy number of plasmids per cell; a kanamycin antibiotic resistance gene, for selection in E. coli.; a pair of BainHI sites surrounding a "stuffer" fragment; flanking T7 and SP6 phage RNA polymerase sites; two rare 8-cutter sites (Not I) flanking the cloning site; an extremely rare Sce I site (from the yeast mating type locus restriction endonuclease), useful for linearizing a library of random inserts without internally cutting the insert; an origin of replication (Epstein Barr Virus replicon, or EBV oriP) that is functional in many eukaryotic cells, including human cells; a lox site useful for integrating DNAs into a genome in a site-specific manner; a drug-resistance gene (blasticidin-S-methylase) that is suitable for eukaryotic cells; as well as an SV40 polyadenylation site, a transcriptional promoter from cytomegalovirus (CMV), and lambda cos ends. PAC vectors such as pCY-PAC2 and pPAC4 are available from any of a number of sources, including RPCI.

C. Preparation of the Library

The library generated will typically represent at least a several fold redundancy of the test genome, i.e., each sequence will be represented, on average, more than once in the library. Preferably, the library will represent at least about, 5, 10, 20, 30, or more fold redundancy. Such redundancy will ensure that a sequence representative of the portion of interest within the genomc is represented at least once in the library, and will also provide additional, higher resolution data regarding the structure of the test genome relative to the reference genome. For a complete human genome, therefore, the number of clones in the library will often be on the order of 30,000, 100,000, 200,000, 400,000, 600,000 or more clones. ESP can, however, be practiced using any number of clones, and any level of redundancy, as even a single clone can be compared to a reference genome to determine a rearrangement in the genome from which the clone was derived. Nevertheless, one of skill will recognize that performing ESP with a large number of clones will greatly improve the resolution and quality of the analysis. For example, while a single discrepancy between a pair of terminal sequences and a corresponding pair of sequences within a reference genome can reflect a valid rearrangement in a test genome, it can also result from technical causes such as recombination within a vector or other artifacts of vector preparation, sequencing errors, or inaccuracies introduced during the preparation or maintenance of a database. Thus, the simultaneous analysis of multiple, overlapping, clones, will provide more robust data, allowing the identification of any type of rearrangement, including those resulting in subtle changes in gene copy number, with a high degree of confidence.

The library is prepared by isolating and preparing genomic DNA (or other test-genome representative nucleic acids) as described supra, isolating and preparing vector DNA, ligating the insert and vector DNA, and transforming bacterial cells with the ligated vector-insert DNA.

In general, vector DNA is obtained using standard methods, e.g., by growing bacterial cells containing the vector, harvesting the cells, lysing the cells (e.g., using lysozyme), removing RNA by adding RNAse, removing insoluble cellular components, precipitating and resuspending the DNA, as well as, e.g., purification with cesium chloride or other methods. See, e.g., Sambrook et al., Ausubel, et al., or any other source of information about plasmid isolation from bacterial cells. Once the vector DNA is isolated, it is linearized using a restriction enzyme and, typically, the 5' phosphates of the linearized vector ends are removed using, e.g., calf intestine phosphatase or bacterial alkaline phosphatase, to prevent vector religation in the absence of an insert.

To perform a ligation, the termini of the insert and the vector must be compatible, which can be accomplished using standard methods. For example, the vector can be digested with the same restriction enzyme used to partially digest the genomic DNA. Alternatively, the vector and genomic DNA can each be prepared for blunt-end ligation, e.g., by cutting with a restriction enzyme that leaves blunt ends, or by mechanically shearing the DNA or cutting with an enzyme that leaves sticky ends, and by filling in the overhanging ends with an appropriate enzyme, e.g., the Kienow fragment of *E. coli* DNA polymerase 1. See, e.g., Sambrook or Ausubel, both supra.

The ligation can be performed using any ratio of insert DNA to vector DNA to achieve optimal ligation. Often, an optimal ratio is determined by performing a series of test ligations using different molar ratios, e.g., 1:10, 1:2, 1:1, 5:1, 10:1, and determining the ratio that gives maximum production of vectors with inserts of desired size. In one preferred embodiment, a vector:insert ratio of 10:1 is used. Ligations are performed under standard conditions, using, e.g., T4 DNA ligase (see, e.g., Ausubel, Sambrook, supra).

Transformation of the host cells are performed according to standard techniques (see, e.g., Morrison, *J. Bact.* 132:349–351 (1977); Clark-Curtiss & Curtiss, *Methods in Enzymology* 101:347–362 (Wu et al., eds, 1983)). Any of the well known procedures for introducing foreign nucleotide sequences into host cells may be used, such as calcium phosphate transfection, polybrene, protoplast fusion, electroporation, liposomes, microinjection, and others (see, e.g., Sambrook et al., supra). In a preferred embodiment, vector-insert DNA is introduced into cells by electroporation. When using PAC or other phage-based libraries, the vectors are packaged and then introduced into cells using standard techniques, including by using any of a large number of commercially available packaging kits.

Any cells can be used to prepare the library. In preferred embodiments, *E. coli* cells such as DH10B (Hanahan et al, 1991), Epicurian Coli® XL10-Gold® Ultracompetent Cells (Stratagene), ElectroTen-Blue™ Electroporation Competent Cells (Stratagene), BMH 71-18 mutS, DH5-alpha, JM109, KC8 (Clontech), HB101, GM8, BL21(DE3)LysS, XL1-blue, SOLR™, SOLR™, DH10B, NM554, and other cells, can be used. See, also, Sambrook, Ausubel, both supra, or, Inoue et al. (1990) *Gene* 96:23–28.

Recombinant transformants are maintained under standard conditions, including, e.g., selection on media containing chloramphenicol, X-Gal, IPTG, kanamycin, saccharin, etc.

D. Isolating Vector-insert DNA

Once the vector is prepared, it is preferably arrayed in multiwell microtiter plates, e.g., plates with 96, 384, or more wells, allowing the automated analysis and manipulation of each of the clones.

Sufficient number of clones (e.g., 50,000 to 250,000 for a human genome) will be generated to ensure sufficient redundancy, and to ensure that one end sequence tag occurs on average every 5, 10, 25, 50, 100, or more kb throughout the genome being studied.

To isolate the vector-insert DNA, the bacterial cells containing the vectors are grown under standard conditions, and the vectors are isolated using standard methods. For example, in a typical embodiment, bacterial cells are cultured, pelleted, and lysed using, e.g., alkaline lysis, and the DNA precipitated, resuspended, and, optionally, cleaned, e.g., by phenol/chloroform extraction.

In addition, any of a number of commercially-available products can be used for isolation of BAC, PAC, P1, and other vectors (either with or without an insert). For example, Magnum columns from Genome Systems, the PSI CLONE BAC Kit, from Princeton Separations Inc., or the Concert High Purity Plasmid Purification Systems from Life Technologies Inc., can be used. Also available is a Large-Construct Kit from QIAGEN, which uses a gravity-flow, anion-exchange column and an ATP-dependent exonuclease to break down genomic DNA. Further, Clontech's Nucleo-Bond Plasmid Kits, based on an anion-exchange column system, can be used. Commercially available BAC/PAC products are also available from any of a number of sources, including RPCI, Research Genetics, CalTech, the Texas A&M BAC Center (hbz.tamu.edu), and others. In addition, companies such as Ana-Gen Technologies Inc., Commonwealth Biotechnologies Inc., Genome Systems, and Research Genetics offer BAC or PAC preparation and/or sequencing. Preferably, multiple samples are processed simultaneously, e.g., using a system such as QIAGEN's R.E.A.L.™ Prep 96 Plasmid Kits, which can either be used with the QIAvac manifold or automated with the BioRobot™ 9600 multipurpose workstation.

It is important to note that any of the herein-described steps can be performed using any of a large number of automated systems. For example, the AutoGen 850 (personal model) and AutoGen 740 (fully automatic) can be used to process BACs, PACs (AutoGen 850), and YACs (AutoGen 850 Alpha). In addition, the BioRobot™ 9600 multipurpose workstation from QIAGEN can be used. Other automated systems include the Packard Multiprobe 204 and 208 robots, which can be used to transfer multiple (e.g., 96) samples at a time.

E. End Sequencing

Once the vector DNA is isolated from the members of the library, the terminal sequences of the inserts are sequenced. Typically, the ends are sequenced using oligonucleotide primers based on T7, SP6, T3, M13, or other primer sequences, and 100, 200, 400, 600, or more nucleotides are sequenced from each terminus. Such primers are well known in the art, and can be synthesized using standard methods or can be ordered from any of a large number of commercial suppliers.

The sequencing of the termini can be performed using any method of DNA sequencing, including Maxam-Gilbert (chemical degradation) and Sanger (chain termination) methods (see, e.g., Sambrook or Ausubel, supra). The templates can be labeled using any method, e.g., radioactive or fluorescent labels, and the labeled products can be separated using any method, such as by polyacrylamide gel electrophoresis, including by high-voltage capillary and ultrathin electrophoresis. Sequencing can involve any method, including the use of resonance ionization spectroscopy to detect stable isotope labels, flow cytometry, direct reading of the base sequence on a DNA strand with the use of scanning tunneling or atomic force microscopies, and enhanced mass spectrometric analysis of DNA sequence. Sequencing can also be performed using high density nucleotide microarrays.

Preferably, the DNA will be sequenced using automated DNA sequencing (see, e.g., Smith et al. (1986) *Nature* 321:674—679). Automated sequencing is not only advantageous in terms of rapidity, efficiency, and accuracy, compared to traditional methods, but it also allows the direct generation of electronically recorded sequence data, thereby facilitating subsequent analysis, e.g., a computer-based comparison with a reference genome.

For automated sequencing, fluorescent dyes are incorporated into a template using any method, e.g., by cycle sequencing (see, e.g., McCombie et al. (1992) *DNA Sequence* 2:289–296), using dye-terminators or by dye-primers, or by using a single reaction including dye-terminators. In a preferred embodiment, the templates are labeled using cycle sequencing and using dye-terminators, such as BigDye from PE Biosystems (Perkin-Elmer). See, e.g., Mahairas et al., (1999) *Proc. Natl. Acad. Sci.* 96:9739–9744).

To perform dideoxy-termination sequencing, DNA templates are replicated in the presence of dideoxynucleotides corresponding to each of A, G, C, and T, whose incorporation into a growing DNA strand results in its termination. Preferably, each of the dideoxynucleotides are labeled with a specific dye, and all four types of dideoxynucleotides are included in a single reaction. Alternatively, the dideoxynucleotides can be individually added to each of four separate reaction mixtures, and the newly synthesized, terminated strands are labeled using either dye-coupled terminators or using labeled primers. Once the specifically labeled, terminated templates are prepared, the reaction (or reactions) are typically loaded into a single lane on an acrylamide slab gel, which allows the analysis of multiple, e.g., 64, lanes simultaneously. During electrophoresis, the dye-labeled DNA fragments separate according to size, and, at the lower portion of the gel, pass beneath a laser beam which excites the fluorescent dyes attached to the fragments and causes them to emit light at a specific wavelength for each dye. This light is then read according to wavelength by a spectrograph onto a cooled, charge coupled device (CCD) camera, so all four types of fluorescent emissions can be detected with one pass of the laser. Data collection software then collects the light intensities using software-selectable filters and stores them as electrical signals for eventual processing.

Any of a number of automated DNA sequencers can be used, such as the Perkin Elmer, Applied Biosystems Division (PE/ABd) 373A or 377 automated DNA sequencers, and can be automatically analyzed using any of a number of software programs, such as the Sequencher Software from Gene Codes as well as the ABI Prism® DNA Sequencing Application Software suite, including Sequencing Analysis Software™, Factura™ Software, and AutoAssembler Software.

IV. Comparing Pairs of Termini with the Reference Genome

Once the termini of the members of the vector library are sequenced, they are compared with a reference genome to compare the co-linearity of the sequences present within the library and corresponding sequences within the reference genome. This analysis is based upon the known physical distance between the two sequences within the vector from the test genome. Such physical distances can be determined in any of a number of ways, including, preferably, by the knowledge of the size range of the inserts within the library, especially when the inserts used to make the library are restricted based on size prior to insertion in the vector, as described supra. In other embodiments, the size of one or more inserts can be determnined, e.g., by determining the size of the vector by gel electrophoresis.

In non-rearranged regions of the genome the order and spacing of the terminal sequence tags will be co-linear with corresponding sequences within the reference genome, and the frequency will be close to that statistically expected for the normal genome copy-number. Deviations in frequency, order, or spacing, however, will reveal rearrangements (including deletions, translocations, amplifications, insertions, and inversions) present in the test genome relative to the reference genome.

To perform the analysis, sequences within the reference genome that correspond to each of the terminal sequences within the library are identified, and the relationship between the members of each pair of corresponding sequences within the reference genome is compared to the relationship between the terminal sequences within the vector. Any difference in the relationship in the reference genome compared to the relationship in the test genome indicates the presence of a rearrangement in the test genome compared to the reference genome. For example, because a pair of terminal sequences within a library is known to be separated by, e.g., 150–200 kb within the test genome (by virtue of their presence at either end of a vector insert), in the absence of any rearrangements a pair of corresponding sequences within the reference genome will also be separated by 150–200 kb. If the corresponding sequences are separated by less than or greater than 150–200 kb, however, then the presence of a rearrangement within the test genome between the two terminal sequences is indicated. Similarly, if the sequences in the reference genome are present on different chromosomes, the presence of a translocation is indicated.

The comparison between the relationship between the terminal sequences and the corresponding sequences within the test genome can indicate any of a large number of potential rearrangements, as will be evident to one of skill in the art. For example, a pair of terminal sequences from the test genome library that are closer than corresponding sequences in the reference genome (or, the corresponding sequences in the reference genome are found to be farther apart than expected based on the known size of the vector insert), indicates the presence of a deletion in the test genome that occurred between the terminal sequences. In contrast, a pair of terminal sequences from the test genome library that are farther apart than corresponding sequences in the reference genome (or, the corresponding sequences within the reference genome are found to be closer together than expected based on the known size of the vector insert) indicates the presence of an insertion within the test genome that occurred between the terminal sequences. Further, a pair of terminal sequences from the test genome that correspond to sequences within the reference genome that are present on different chromosomes indicates the presence of a translocation within the test genome that occurred between the terminal sequences. The present methods can also be used to identify amplifications, e.g., duplications, of sequences. Specifically, a terminal sequence that falls within an amplified region will be present within the library at a greater than normal frequency (i.e., there will be more "hits," or corresponding sequences, identified within an amplified region of the genome). In contrast, a termninal sequence falling within a heterozygous or homozygous deletion will be present at a lower than expected frequency (i.e., there will be fewer "hits," or corresponding sequences, identified within the region of the genome affected by the deletion or deletions). Thus, both the physical relationship between as well as the frequency of each pair of terminal sequences will allow the detection of any type of rearrangement.

It will be recognized thal, particularly when comparing related species or strains, ESP analysis can just as simply indicate the presence of a rearrangement that occurred in the reference genome rather than the test genome. For example, when comparing human and chimpanzee genomes, although the human genome will likely represent the "reference genome" for the analysis, any rearrangements identified will likely represent rearrangements that occurred in the human (i.e., reference) genome during human evolution.

ESP analysis is greatly aided by the fact thal, due to the high level of redundancy within the library, each region of the test genome is covered by a large number of overlapping inserts, i.e., a terminal sequence will be present, on average, as often as every 5–10 kb throughout the test genome or genomic region. Thus, any deletions, insertions, amplifications, etc. will affect a substantial number of overlapping inserts. For example, in the case of a deletion or insertion, every insert that spans the site of the rearrangement (e.g., for a library comprising inserts of 150 kb, with termini spaced every 5 kb, a total of approximately 30 overlapping inserts should be affected by the rearrangement) will show a corresponding change when its terminal sequences are compared with the reference genome. Such correspondence among overlapping clones will provide confirmation of a single discrepancy, and will greatly increase the robustness of the data generated from an ESP analysis, thereby allowing the detection and statistical confirmation of even small-scale changes such as small deletions, small inversions, small insertions, and small-scale amplifications.

Many aspects, and preferably all aspects, of an ESP analysis will be performed using a computer. For example, once a pair of terminal sequences has been identified, corresponding sequences within the reference genome are typically identified using a suitable algorithm such as BLAST (see, e.g., the BLAST server at the National Center for Biotechnology Information; http://www.ncbi.nlm.nih.gov/). A BLAST or equivalent search will identify corresponding sequences within a reference genome, preferably ranked in order of similarity to the terminal sequence. In many cases, the identification of the corresponding sequence will be unambiguous, for example only a single sequence within the reference genome will show significant identity to the terminal sequence. In other cases, however, a number of sequences will be identified that show homology to the terminal sequence. In that case, usually the sequence with the highest percent sequence identity will be identified as the true corresponding sequence. Other information can be relied upon to resolve ambiguity as well, for example, if a sequence from the reference genome that potentially corresponds to one terminal sequence from a vector is separated by, e.g., 150–200 kb from a second sequence within the reference genome that clearly corresponds to the other terminal sequence within the same vector, then the first, potential corresponding sequence will typically be concluded to represent the true corresponding sequence.

In a preferred embodiment, the ESP analysis will be limited to unique sequences within the test genome. This can be accomplished in any standard way, for example by using a program such as RepeatMasker (University of Washington Genome Center, Seattle, Wash.) to eliminate known repetitive sequences from the analysis.

Typically, the computer will determine the co-linearity between each pair of terminal sequences within the test genome library and a pair of corresponding sequences within the reference genome, thereby identifying each vector, and hence each region within the test genome, that is different from the reference genome. Because, as described supra, each rearrangement within the test genome should affect a number of overlapping vector inserts, each vector that shows a discrepancy with the reference genome should have a number of overlapping clones that also show a discrepancy. The computer will typically thus integrate the data from each vector, and, e.g., by testing various models (i.e., what kind of rearrangement can account for the various pairs of terminal sequences observed, taking into account the presence of two homologous chromosomes in a diploid organism, etc.), will identify a "best" explanation, i.e., will posit a particular rearrangement, or set of rearrangements, that can account for each of the discrepancies between the pairs of terminal sequences within a given region and the corresponding sequences within the reference genome from the same region. In this way, the computer can create a detailed map of all of the rearrangements within the test genome that is supported by a large amount of data.

In some embodiments, the data representing the distribution of sequences within the reference genome (or the test genome, if, e.g., "chromosome" maps are constructed for the test genome based on overlapping vector sequences) corresponding to each pair of terminal sequences is presented in visual form. In a typical embodiment, each corresponding sequence identified within the reference genome is plotted along an axis with appropriate scale marks. The density of corresponding sequences is calculated per given window (i.e., within a given genomic interval of the reference genome) and each of the hits (i.e., corresponding sequences) is represented as a circle on one side of the axis in the appropriate interval. These circles are color-coded according to their position within the reference genome (e.g., according to their genomic position; alternatively, the circles can be coded according to their position within the test genome, if test genome maps are generated, as described supra). Additionally, on the other side of the axis, lines are used to connect sequences corresponding to each member of a pair of terminal sequences, i.e., to delineate the relationship between each pair of corresponding sequences within the test genome. The advantage of this type of presentation is that (a) it gives immediate visual clues regarding the position of putative rearrangements (found as e.g., changes in the number of insert ends, unusual relationships between linked terminal sequences, color of the circles, etc.) and (b) it can be easily integrated with independently-developed sequence analysis software.

To perform ESP, the reference genome can be any genomc that is substantially sequenced and which is present in a searchable database. For example, a large number of sequenced genomes are accessible from a number of genome databases, for example from the National Center for Biotechnology Information, the Institute for Genomic Research (TIGR), the National Agricultural Library, FlyBase, BeanGenes (A Phaseolus/Vigna sp. Database), ACEDB (A Caenorhabditis elegans DataBase), the Bacillus subtilis genome sequencing project, the Genome Sequence DataBase at the NCGR (National Center for Genome Resources), ChickGBASE, the Influenza Sequence Database at Los Alamos National Laboratory, Saccharomyces Genome Database, the RATMAP (The Rat Genome Database), the Genome Database (GDB) from the Human Genome Initiative, the National Animal Genome Research Program (NAGRP), NSF Plant Genome Projects, the Jackson Laboratory, Celera, and many others.

Once a pair of sequences corresponding to a pair of terminal sequences are identified within the reference genome, the relationship between the genomic location of the sequences is determined and compared to the relationship between the pair of terminal sequences. Although, if performed using a small number of clones, this step can be performed manually, it is preferably carried out using a computer. Most preferably, a computer will be used to perform such analysis simultaneously for a large number of clones (e.g., the entire library), and will integrate the data generated from each pair of terminal sequences to generate a map showing all of the detected rearrangements. In one embodiment, a map of the entire test genome is generated, showing the location of the terminal sequences within the test genome, and, for each terminal sequence, showing the corresponding genomic location of the homologous sequence from the reference genome. Alternatively, the analysis will produce a map of the reference genome, showing the location of each pair of terminal sequences within the reference genome. In either case, the result of the analysis will be a map, or set of maps, clearly showing the location and nature of each genomic difference, e.g., rearrangement, between the test genome and the reference genome.

V. Determining Breakpoints

Once a map of all of the rearrangements present in the test genome relative to the reference genome is generated, it will often be desirable to sequence the DNA corresponding to each of the rearrangements, i.e., to sequence at least one clone or subclone spanning at least one of the breakpoints of the rearrangement. As described infra, such breakpoint-containing regions will often contain chimeric genes, gene mutations or deletions, or gene amplifications, that play an important role in the progression of diseases such as cancer, or in the establishment of differences between species or strains. Accordingly, the sequencing of such genes will allow the development of novel diagnostic and therapeutic tools for any of a number of diseases, and will provide important tools for the understanding of any of a number of differences between species or strains.

Rearrangements often place genomic sequences in proximity that were previously separated within the same chromosome, or present on different chromosomes. For example, a deletion brings the sequences flanking the deletion breakpoints together, and translocations brings sequences previously on different chromosomes in close proximity. The results of such rearrangements can have a profound impact on a cell or an organism. For example, in a tumor cell, a breakpoint can place a sequence coding for a cell cycle-driving protein in close proximity with a regulatory element that drives its ectopic or unregulated expression, thereby provoking increased proliferation of the cell. Further, a rearrangement can create chimeric genes, containing portions of previously separated coding sequences, that encode new fusion proteins. Such fusion proteins can be, e.g., under the control of new regulatory mechanisms, can have novel activity or binding affinity to heterologous proteins, or can have any other alteration in any property that can contribute to, e.g., cancer progression. Rearrangements also commonly remove gene function, for example by deleting one or more genes, or by virtue of a breakpoint that interrupts a gene in a way that prevents its expression or function. Such loss of gene function can have obvious effects on cellular behavior and phenotype.

Accordingly, once rearrangements have been identified within a test genome using ESP, the DNA surrounding at least one of the breakpoints is sequenced. For example, one or more clones, or portions of a clone, that span the rearrangement breakpoint are sequenced. In this way, any fusion proteins, misregulated genes, chimeric genes, deletions, interrupted genes, etc. can be identified.

The sequencing of any clone, or portion of a clone, corresponding to a breakpoint can be performed using any standard method, e.g., by subcloning the insert into smaller plasmid vectors and sequencing the vectors using the herein-described methods.

VI. EXAMPLES

A. Example I—ESP within known Regions of Genomic Amplification

ESP is performed on a small scale to identify chromosomal rearrangements within known regions of genomic amplification in a well characterized breast cancer cell line.

A 30-fold redundant BAC library from the breast cancer cell line MCF7 is generated and arrayed, and clones carrying genes known to be amplified in this cell line, such as AIB1, ERRB2, and ZNF217, are selected.

The termini of the inserts within several hundred BACs carrying these genes are sequenced, e.g., in collaboration with a genome center capable of high throughput sequencing.

Custom genome analysis software is applied to the resulting sequence data to identify: (a) structural rearrangements in the MCF7 genome within BACs carrying oncogenes such as AIB1, ERRB2, and ZNF217, (b) mutations in the BAC end sequences, (c) genes that are brought into close proximity to ERRB2, MYC, and ZNF217 as a result of structural rearrangements.

Any BACs spanning structural rearrangements are sequenced to identify the sequences involved in the rearrangement.

B. Example II—Evaluation of Software Using Publicly Available BAC end Sequences Computational tools are developed in a draft form for ESP analysis, and their utility is evaluated by aligning publicly available BAC end sequences (Mahairas et al., (1999) *PNAS* 17:9739–44) from the GSS database (http://www.ncbi.nlm.nih.gov:80/blast/blast.cgi?Jform=0) to genomic sequence covering 1.5 Mb of chromosome 20q13.2 that has been sequenced in collaboration with the Joint Genome Institute from the Department of Energy (http://wwwjgi.doe.gov/).

While the foregoing invention has been described in some detail for purposes of clarity and understanding, it will be clear to one skilled in the art from a reading of this disclosure that various changes in form and detail can be made without departing from the true scope of the invention. For example, all the techniques and apparatus described above may be used in various combinations. All publications and patent documents cited in this application are incorporated by reference in their entirety for all purposes to the same extent as if each individual publication or patent document were so individually denoted.

What is claimed is:

1. A method for comparing a test genome to a reference genome, said method comprising:
   (i) providing a plurality of clones of known size that substantially cover at least a portion of said test genome;
   (ii) obtaining sequence information from the termini of each of said plurality of clones, thereby obtaining a pair of terminal sequences;
   (iii) identifying a pair of sequences within said reference genome that corresponds to each of said pairs of terminal sequences; and
   (iv) determining the relationship between the members of each pair of corresponding sequences within said reference genome;
   wherein a difference in the observed relationship between the members of any of said pairs of corresponding sequences within said reference genome and the expected relationship based upon said known size of said plurality of clones indicates the presence of a rearrangement in said test genome compared to said reference genome and wherein said test genome is obtained from an individual with a disease associated with chromosomal rearrangements.

2. The method of claim 1, further comprising determining the sequence of said test genome over a region spanning at least one breakpoint of said rearrangement.

3. The method of claim 1, wherein said reference genome is a human genome.

4. The method of claim 1, wherein said test genome is from a tumor cell.

5. The method of claim 1, wherein said reference genome and said test genome are from different species.

6. The method of claim 1, wherein said plurality of clones covers substantially all of said test genome.

7. The method of claim 1, further comprising determining the frequency of each of said terminal sequences within said plurality of clones, wherein an increased or decreased relative frequency of any of said terminal sequences indicates the presence of an amplification or a deletion in said test genome that includes said terminal sequence.

8. The method of claim 1, wherein said plurality of clones are BAC clones.

9. The method of claim 1, wherein said plurality of clones are PAC clones.

10. The method of claim 1, wherein said plurality of clones represents a redundancy of at least about 10 fold of said test genome or said portion of said test genome.

11. The method of claim 10, wherein said plurality of clones represents a redundancy of at least about 20 fold of said test genome or said portion of said test genome.

12. The method of claim 1, wherein said terminal sequences are present on average between about every 5 kb to about every 500 kb throughout said test genome or said portion of said test genome.

13. The method of claim 12, wherein said terminal sequences are present on average every 50 kb or less throughout said test genome or said portion of said test genome.

14. The method of claim 13, wherein said terminal sequences are present on average every 10 kb or less throughout said test genome or said portion of said test genome.

15. The method of claim 14, wherein said terminal sequences are present on average every 5 kb or less throughout said test genome or said portion of said test genome.

16. The method of claim 1, wherein said reference genome is a human genome, and wherein said plurality of clones comprises at least about 100,000 clones.

17. The method of claim 16, wherein said plurality of clones comprises at least about 200,000 clones.

18. The method of claim 17, wherein said plurality of clones comprises at least about 250,000 clones.

19. The method of claim 1, wherein said terminal sequences are determined by automated sequencing.

20. The method of claim 1, wherein said pairs of terminal sequences from said test genome are compared to said pairs of corresponding sequences within said reference genome using a computer.

21. The method of claim 1, wherein the determining step (iv) comprises determining the genetic or physical distance the pair of sequences.

22. The method of claim 1, wherein the determining step (iv) comprises determining whether the pair of sequences are present in the same vector or chromosome.

23. The method of claim 1, wherein the reference genome is substantially sequenced and is present in a searchable database and the pair of sequences within said reference genome that corresponds to each of said pairs of terminal sequences are identified by comparing the terminal sequences to the reference genome using a computer.

24. The method of claim 1, wherein the clones are cDNA clones.

* * * * *